United States Patent
Beedall et al.

(10) Patent No.: US 8,597,302 B2
(45) Date of Patent: Dec. 3, 2013

(54) SURGICAL INSTRUMENT

(75) Inventors: Duncan Beedall, Leeds (GB); David Fisher, Fishers, IN (US); Sourav Ghosh, Leeds (GB)

(73) Assignee: Depuy (Ireland) (IE)

( * ) Notice: Subject to any disclaimer, the term of this patent is extended or adjusted under 35 U.S.C. 154(b) by 137 days.

(21) Appl. No.: 13/379,518

(22) PCT Filed: Jul. 1, 2010

(86) PCT No.: PCT/GB2010/001278
§ 371 (c)(1),
(2), (4) Date: Jan. 18, 2012

(87) PCT Pub. No.: WO2011/004140
PCT Pub. Date: Jan. 13, 2011

(65) Prior Publication Data
US 2012/0123429 A1    May 17, 2012

(30) Foreign Application Priority Data
Jul. 4, 2009 (GB) .................... 0911643.5

(51) Int. Cl.
*A61B 17/58* (2006.01)
*A61B 17/60* (2006.01)
*A61F 2/00* (2006.01)

(52) U.S. Cl.
USPC .......... 606/99; 606/88; 623/20.14; 623/20.31

(58) Field of Classification Search
USPC .................. 606/88, 99, 79, 86 R, 86 A, 86 B
See application file for complete search history.

(56) References Cited

U.S. PATENT DOCUMENTS

| | | | |
|---|---|---|---|
| 5,059,196 A * | 10/1991 | Coates | 606/99 |
| 5,062,852 A | 11/1991 | Dorr | |
| D337,639 S * | 7/1993 | Beckman | D24/133 |
| 5,571,111 A | 11/1996 | Aboczky | |
| 5,732,992 A | 3/1998 | Mauldin | |
| 5,902,339 A * | 5/1999 | Keller | 623/20.31 |
| 2003/0109929 A1* | 6/2003 | Keller | 623/20.14 |
| 2006/0116769 A1 | 6/2006 | Marnay | |

FOREIGN PATENT DOCUMENTS

| | | |
|---|---|---|
| DE | 10013331 A1 | 9/2001 |
| EP | 780090 A1 | 6/1997 |
| WO | WO 9325164 A1 | 12/1993 |

OTHER PUBLICATIONS

PCT International Search Report PCT/GB2010/001278 dated Feb. 21, 2011.
UK Search Report GB0911643.5 search date Aug. 20, 2009.

* cited by examiner

*Primary Examiner* — Sameh Boles
*Assistant Examiner* — Samuel Hanna

(57) ABSTRACT

A multi-function impactor for use with an orthopaedic implant, such as a knee joint, is described. The head of the impactor has a pair of curved recesses for mating with condylar parts of a femoral implant and flat faces for mating with a tibial implant. An extended formation is also provided for use with the inter-condylar notch of the femoral implant. A v-shaped notch in the extended formation is also provided to impact a tibial insert. The impactor can be made from a single moulded plastics part.

4 Claims, 3 Drawing Sheets

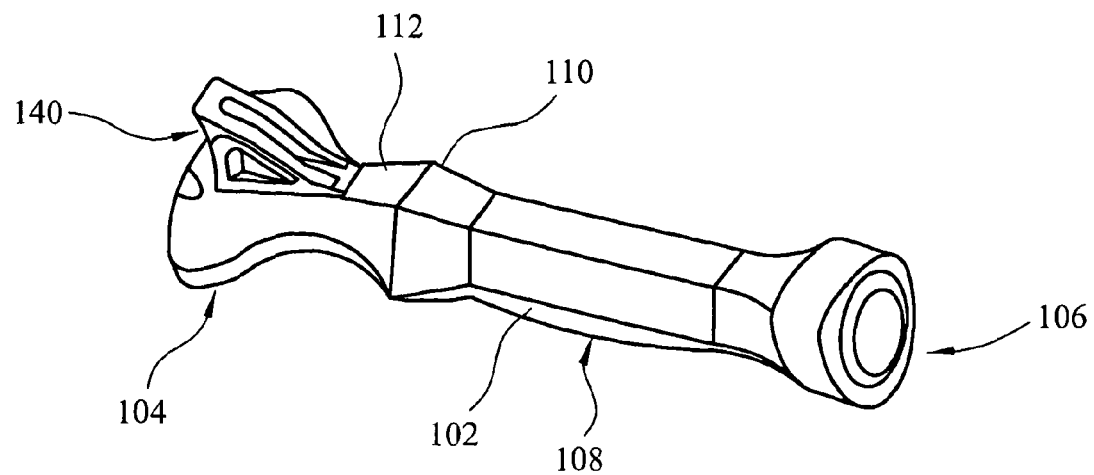
FIG. 1
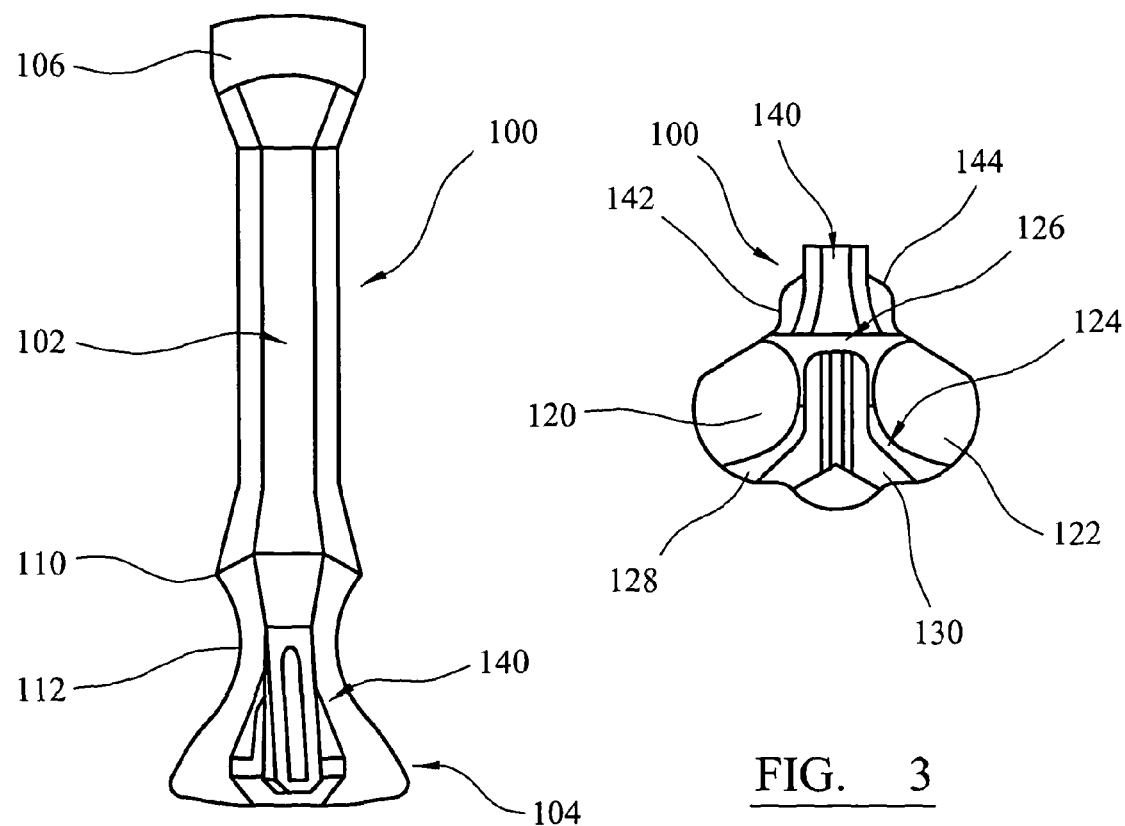
FIG. 2
FIG. 3

US 8,597,302 B2

SURGICAL INSTRUMENT

CROSS REFERENCE TO RELATED APPLICATION

This application is a National Stage 35 U.S.C. 371 of International Patent Application PCT/GB2010/001278 filed Jul. 1, 2010

BACKGROUND OF THE INVENTION

The present invention relates to a surgical instrument, and in particular to an impactor for use with orthopaedic implants.

Impactors are used during orthopaedic arthroplasty procedures to drive the implant components onto the bone. Often bone cement is also used to secure the implant to the bone, but there is usually a tight or interference fit between the implant component. Hence, a tool, such as a mallet, hammer or similar, is used to drive the implant component onto the bone, by hitting a free end of the impactor, while the impactor engages the implant. However, it is important to ensure that an even pressure is applied to the component, so that it seats correctly on the resected bone surface, and also that the bearing surfaces are not damaged during impaction. Hence, different impactors can be needed in order to impact the same or different implant components, so that they are correctly seated and damage is avoided.

Impactors are used during orthopaedic arthroplasty procedures to drive the implant components onto the bone. Often bone cement is also used to secure the implant to the bone, but there is usually a tight or interference fit between the implant component. Hence, a tool, such as a mallet, hammer or similar, is used to drive the implant component onto the bone, by hitting a free end of the impactor, while the impactor engages the implant. However, it is important to ensure that an even pressure is applied to the component, so that it seats correctly on the resected bone surface, and also that the bearing surfaces are not damaged during impaction. Hence, different impactors can be needed in order to impact the same or different implant components, so that they are correctly seated and damage is avoided.

For example, an impactor exists which has a handle and a plurality of releasably attachable head parts. The head parts and the handle have an attachment mechanism which allows the heads to be interchanged on the handle. A head configured to impact a femoral component of an artificial knee joint can be provided, together with a headed configured to operate on the notch of the femoral component and also a head configured to operate on a tibial component. However, use of such an impactor can cause delays in the surgical procedure as it is necessary to swap the heads. Also, such devices are more complex to manufacture and use and can be difficult to sterilise owing to the mechanical attachment mechanism for the different heads.

Also, some of impactor heads can be attached to the implants, but then tend to be useable only with a specific implant and again are more complex to manufacture and harder to sterilise.

More simple impaction devices are also available which can be used generally for impaction but do not have any inbuilt features to perform the specific impaction tasks required. This can lead to damage of the implant components due to scratching of the bearing surfaces and/or deformations and hence have limited utility.

Hence, there is a need for a multifunction impactor which can more easily be used to reliably impact orthopaedic implants.

BRIEF SUMMARY OF THE INVENTION

According to a first aspect of the present invention, there is provided a multi-function impactor for use with an orthopaedic implant having a plurality of different components, the impactor comprising: a shaft and having a proximal end impactable with a tool by a user; and a head at a distal end of the shaft, wherein the head has a first formation shaped to match a portion of a first component of the orthopaedic implant and a second formation shaped to match a portion of a second component of the orthopaedic implant.

Hence, the same impactor can be used to impact different components of the orthopaedic implant as the impactor head includes formations specifically configured to mate with or abut specific portions of the different components of the orthopaedic implant.

The shaft, or a part of the shaft, can form a handle for the impactor.

The orthopaedic implant can have various numbers of different components, such as two, three, four or more than four.

The orthopaedic implant can be a knee implant. The knee implant can comprise or include at least a femoral component and/or a tibial component and/or a tibial insert component.

The first formation can include at least one curved surface. The first formation can comprise two curved surfaces. The curved surfaces can be concave surfaces. The curved surfaces can curve in at least two directions. They can have a uniform or non-uniform curvature in each or all directions. The curved surfaces can be arranged in a pair. The pair can be disposed to either side of a central axis of the head. The curved surface or surfaces can be configured, positioned and/or sized to mate with, conform to or generally match at least a portion of the condylar part or parts of a femoral component of the orthopaedic implant.

The second formation can comprise at least a first flat surface. Preferably the second formation comprises at least two flat coplanar surfaces. The flat coplanar surfaces can be disposed on either side of a central axis of the head. The second formation can include a third flat surface, which is coplanar with the other two. The three flat coplanar surfaces can be disposed in a generally triangular configuration. A top one of the three can be disposed generally on the central axis of the head and the other two can be disposed to either side of the central axis. The flat surfaces can between them define a recessed portion of the head for receiving a portion of a tibial component. The second component of the orthopaedic implant can be a tibial component of the orthopaedic implant. The flat surface or surfaces can be configured, positioned and/or sized to mate with or generally match an upper surface of a tibial component so as to apply a generally uniform pressure thereto when the impactor is struck in use.

The head can further include a third formation. The third formation can be shaped to engage with a further portion of one of the components of the orthopaedic implant. The third formation can extend proud of the head. The third formation can extend from a front part of the head. The third part can be a notch of a femoral component of the orthopaedic implant. A free end of the third part can be configured, positioned, shaped and/or sized to engage in the inter-condylar notch of a femoral component.

The impactor can further comprising a fourth formation shaped to engage a portion of a one of the components of the orthopaedic implant. The fourth formation can be a notch.

The fourth formation can be generally V-shaped. The notch can be in an implant facing surface. The implant facing surface can be part of a formation that extends proud of the head. The formation can be the third formation. The notch can be shaped to receive part or portion of a tibial insert, and in particular an edge of a tibial insert. The implant can include a further tibial component and in particular a tibial insert component. The notch can be shaped, sized and/or configured to retain an edge of the tibial component within the notch when an impaction force is applied to the tibial component by striking the impactor.

The head can be an integral part of the shaft. That is the head can be unitary to the shaft part of the impactor. The entire impactor can have a unitary construction. That is the impactor can be made from a single part. This avoids any moving parts and hence makes the impactor easier to clean or sterilise. This also makes manufacture of the impactor simpler and cheaper. For example, the impactor can be moulded. The impactor can be from a plastics material, for example an impact resistant polymer such as a polycarbonate or a polyphenylsulfone (PPSu).

According to a second aspect of the invention, there is provided a multi-function moulded plastics impactor for use with an orthopaedic implant. The multi-function impactor can comprise a head having a first formation shaped to match a first part of the orthopaedic implant and a second formation shaped to match a second part of the orthopaedic implant.

Preferred features of the first aspect of the invention can also be preferred features of the second aspect of the invention.

A third aspect of the invention provides a method of impacting an orthopaedic implant using an impactor. The orthopaedic implant can be impacted by engaging a first formation of a head of the impactor with a first portion of the orthopaedic implant. The orthopaedic implant can be impacted by engaging a second formation of the head of the impactor with a second portion of the orthopaedic implant.

As different formations of the same head are used to engage different portions of the same or different components of the orthopaedic implant, the same impactor can be used to reliably impact the orthopaedic implant.

The first and second portions can be of different components or the same component of the orthopaedic implant.

The first formation can comprise curved surfaces. The first portion of the orthopaedic implant can be the condyles of a femoral component of the orthopaedic implant.

The second formation can comprise at least a pair of flat coplanar surfaces. The second portion of the orthopaedic implant can be a tibial component of the orthopaedic implant.

The method can further comprise impacting the orthopaedic implant by engaging a third formation of the head of the impactor with a third portion of the orthopaedic implant.

The third formation can extend proud of the head. The third portion can be a notch of a femoral component of the orthopaedic implant.

The method can further comprise impacting the orthopaedic implant by engaging a fourth formation of the head of the impactor with a further portion of a one of the components of the orthopaedic implant. The fourth component can be a tibial component such as a tibial insert. The fourth component can be a notch, such as a generally V-shaped notch.

BRIEF DESCRIPTION OF THE DRAWINGS

Embodiments of the invention will now be described, by way of example only, and with reference to the accompanying drawings, in which:

FIG. 1 shows a perspective view of a first embodiment of a multifunction impactor according to the present invention;

FIG. 2 shows a side view of the impactor shown in FIG. 1;

FIG. 3 shows an end view illustrating the head of the impactor shown in FIG. 1;

Figure 4:
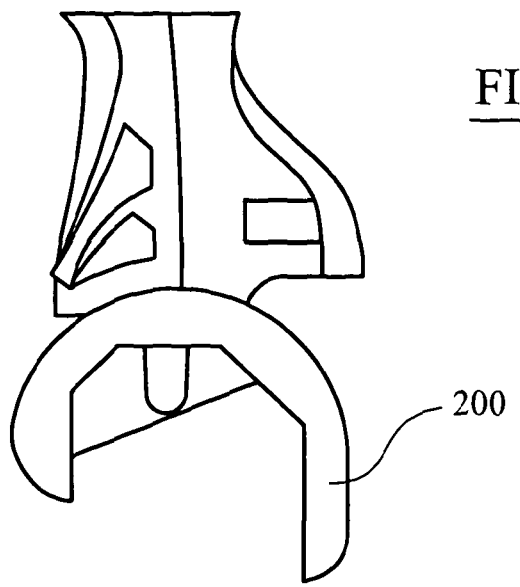
FIG. 4 shows a side view of the impactor in use and engaging the condyles of a femoral component of an orthopaedic implant.

Similar items in different Figures share common reference numerals unless indicated otherwise.

DETAILED DESCRIPTION OF THE INVENTION

With reference to FIG. 1 there is shown a multi-function impactor 100 according to the present invention. The impactor 100 generally has a central shaft portion 102 and has a head 104 at a first distal end and also has a second proximal end 106. The second end 106 has a generally rounded triangular form with a central slightly raised circular portion which provides a strike zone for receiving a blow from a tool, such as a hammer or mallet, in use. A portion of the shaft below the second end forms a handle by which the impactor can be gasped in use. The handle portion of the shaft has a slightly bulging portion 108 to facilitate grip thereof by the user. A slightly thicker, flared portion 110 defines the lower part of the handle and the shaft then narrows to a neck region 112 before flaring into the impactor head 104.

As can best be seen in FIG. 3, the impactor head 104 has a number of formations which are shaped, spaced, sized, positioned and otherwise configured to engage with different parts of an orthopaedic implant during use of the impactor 100.

The impactor head 104 includes a pair of formations 120, 122 in the form of curved concave recesses disposed on either side of the central longitudinal axis of the impactor. These curved recess portions 120, 122 are shaped and sized to generally conform with the curved condylar portions of a typical femoral component of a knee prosthesis, as will be described in greater detail below with reference to FIG. 4.

Impactor head 104 also includes a second formation in the form of three flat, co-planar surfaces 124, 126, 128 which together define a shallow channel 130 with a flared open end between them. As can be seen from FIG. 3, flat surfaces 128 and 124 sit either side of the central axis, and toward a rear side, of the head and flat surface 126 is positioned at the closed end of channel 130, on the central axis and toward a front side of the head. The flat portions 124, 126 and 128 have a generally triangular layout and between them provide a flat co-planar surface for engaging with a tibial component of an implant as will be described in greater detail below with reference to FIG. 6. Further, recess 130 can receive any proud parts or features of the tibial component in use.

The impactor head 104 also includes a third formation 140 extending from a front side of the impactor head. The third formation 140 is generally in the form of an extended member standing proud from the frontal surface of the head and having strengthening portions 142, 144 to either side. The third formation 140 is shaped, sized and configured to be received within the notch of a femoral component as will be described in greater detail below with reference to FIG. 5.

As shown in FIGS. 1, 2 and 3, the impactor 100 has a unitary construction, that is it is not made from separate individual parts. In particular, the impactor is moulded as a single part from a plastics material, such as a highly impact resistant polymer. For example, the impactor can be made from a ploycarbonate such as Makrolon as provided by Bayer Corporation. The impactor can also be made from a polyphenylsulfone (PPSu) such as Radel as provided by Solvay SA.

Use of the impactor 100 during a total knee replacement surgical procedure will now briefly be described with reference to FIGS. 4, 5 and 6. After re-section of the femur and tibia, and appropriate sizing of the femoral and tibial components using trial components, the impactor is used to place the orthopaedic implant components on the patient's resected bone. Often, bone cement is also be used to help secure the implant components in place. Although a specific workflow will be described in the following, it will be appreciated that the invention is not limited to this specific workflow and the impactor can be used in any sequence of steps as preferred by the surgeon and depending on the particular surgical procedure being carried out.

Figure 5:
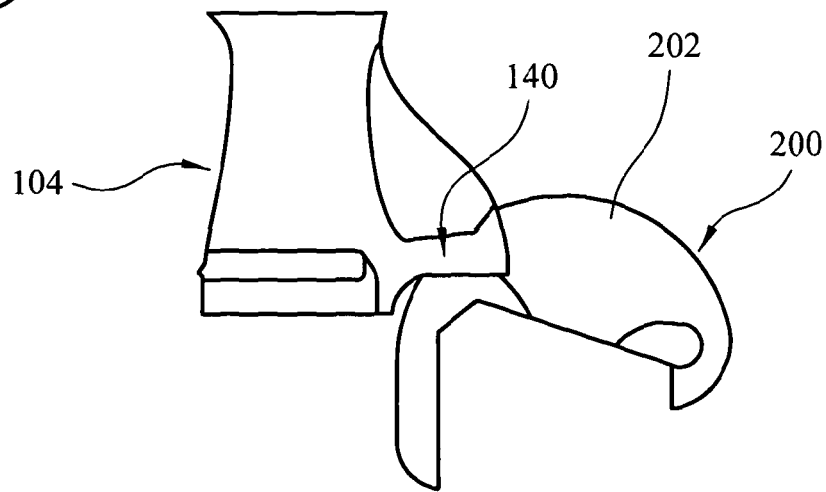
FIG. 5 shows a side view of the impactor in use and engaging the notch of a femoral component of an orthopaedic implant.

FIG. 4 shows a side view of a femoral component 200 of a replacement knee prosthesis. The implant component 200 is placed on the resected femur and the pair of curved recessed formations 120, 122 are respectively engaged with the corresponding curved condylar portions of the femoral component. The proximal end of the impactor 100 is then struck by the surgeon so as to drive the femoral component onto the femur.

The impactor head is then removed from the femoral component and the impactor is rotated by 180° about its longitudinal axis and the free end of the extended formation 140 introduced into the gap or notch typically found between the condylar portions of a femoral implant. FIG. 5 shows a cross-section through the head part of the impactor 104 and through the femoral component 200 and shows the extended formation 140 engaged with a part of the femoral component in the notch formed between the condylar components, only one of which 202 can be seen in FIG. 5. The surgeon again uses the tool to impact the proximal free end 106 of the impactor so as to drive the femoral component 200 onto the resected femur. This impaction can sometimes be required in order to "rock" the femoral component so that it is correctly fully seated on the resected femur.

Figure 6:
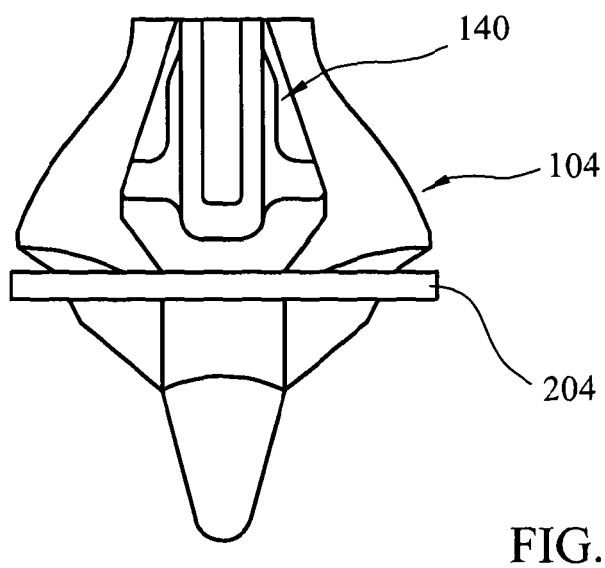
FIG. 6 shows a front view of the impactor in use with the tibial component of an orthopaedic implant.

The impactor 100 can then be used to drive the tibial component 204 into the resected and reamed tibia as illustrated in FIG. 6. FIG. 6 shows a view from a front side of the head of the impactor 104, in which the three flat co-planar formations 124, 126, 128 are all engaged with or abut the flat upper surface of the tibial component 204. The tibial component is also sometimes referred to as the tibial tray. Again, a tool, such as a mallet, is used to strike the free end of the impactor so as to drive the tibial component 204 into a cavity reamed in the tibia until the lower surface of the tibial component is correctly seated against the upper resected surface of the tibia.

Hence, as described above, the same impactor 100 can be used to impact the different implant components of a knee joint in an easy to use and reliable manner, without damaging the implant components.

The head of the impactor has three dedicated impaction areas for femoral impaction, notch impaction and tibial impaction. The curved recesses are designed and shaped to provide a best fit congruent surface for a variety of sizes of femoral implants. The best-fit surface ensures contact points with a large range of sizes of femoral implants so that the implants can be accurately guided into position during impaction. Further, an integrated notch impaction feature is provided in the impactor head which can be effectively used to impact the box of a variety of sizes of femoral implants, particularly posterior stabilised implants. Furthermore, the flat impaction areas 124, 126, 128 allow the impaction of a variety of sizes of both fixed bearing and mobile bearing tibial trays. The flat, symmetrical impaction areas transmit the impaction load over a large surface area and help reduce any damage to the tray during impaction. Further, the flat contact areas are balanced over the face of the head to distribute the load and guide the tibial tray accurately into position during impaction.

As the impactor is manufactured from a single moulded piece of plastic it is very cheap to produce and facilitates the production of a very cost effective instrument set.

Figure 7:
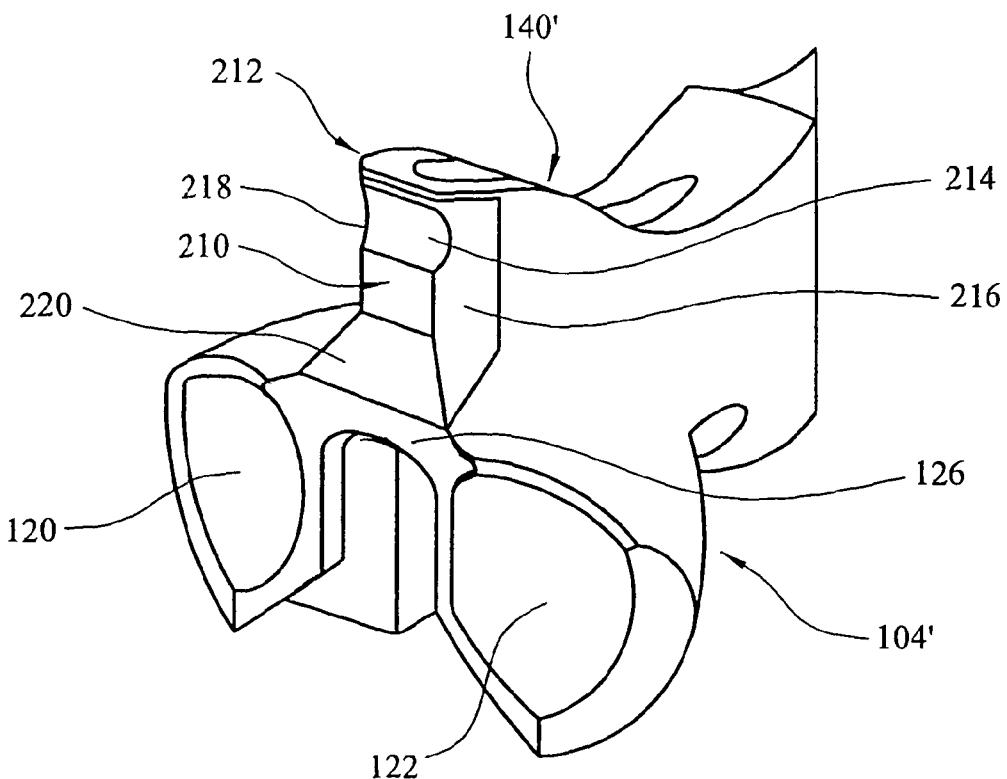
FIG. 7 shows a perspective view of a head of a second embodiment of the impactor of the invention.

FIG. 7 shows a perspective view of a head part 104' of a second embodiment of an impactor according to the invention. Head part 104' is generally similar to the head part 104 of the first embodiment of the invention shown in the preceding Figures. However, as shown in FIG. 7, the third formation 140' is slightly modified compared to the third formation 140 of the first embodiment. In particular an implant facing underside 210 of the extended member 212 includes a generally V-shaped notch, trough, channel or generally concave formation 214 extending across the width of the extended member 212. The V-shaped concave formation 214 is located toward the free end of extended member 212. The V-shaped concave formation is located in the generally flat underside 210 of the extended member and a respective chamfered surface 216, 218 is located at each end of the V-shaped notch so that the width of the implant facing surface 210 portion is less than the overall width of the extended member. Put another way, the lower portion of extended member 212 has a generally trapezoid cross sectional shape. As also shown in FIG. 7, the lower surface 210 is off set along the longitudinal axis of the instrument away from flat face 126 and is connected thereto by curved surface 220.

Figure 8:
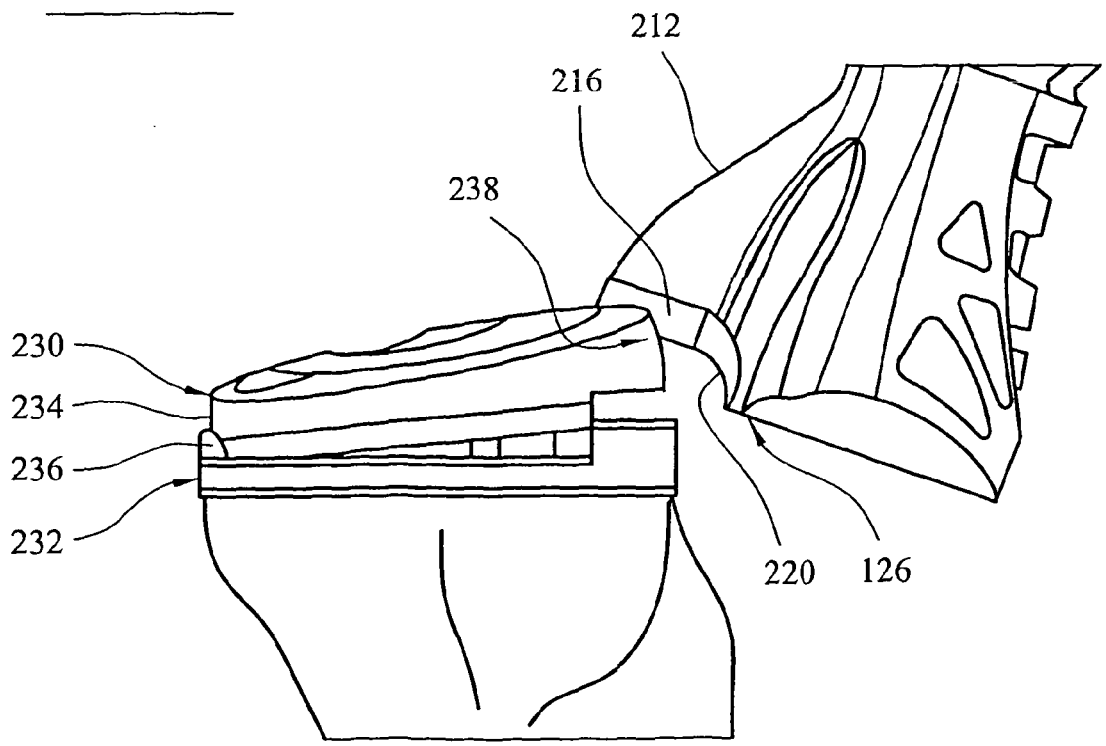
FIG. 8 illustrates use of the second embodiment of the impactor to insert a tibial part of an orthopaedic implant.

V-shaped notch 214 is shaped, sized and otherwise configured to receive an edge portion of a further component of the knee implant and in particular a tibial insert component 230, as illustrated in FIG. 8. FIG. 8 shows a side view illustrating use of the second embodiment of the impactor to impact a tibial insert component 230 into a tibial tray component of a knee implant. The tibial insert component can be for example a plastics component which provides a bearing surface on which the condyles of the femoral component can bear. The tibial component might also be a spacer or act as a spacer for the knee joint.

As illustrated in FIG. 8, after the tibial tray component has been impacted using the flat faces of the impactor (as described above), the tibial insert component can also be inserted using the impactor. A posterior part 234 of the insert 230 abuts against a posterior formation 236 of the tibial tray and an anterior edge portion 238 of the insert is positioned in the V-shaped notch 214 of the impactor head 104'. The end of the impactor can be struck to apply an impaction force to securely seat insert 230 in the tibial tray 232. V-shaped notch 214 safely retains edge 238 of the insert and so helps to appropriate direct force toward the insert and prevents the insert slipping out of contact with the impactor when the impaction force is applied. Otherwise, if the insert slips, then the curved surface portion 220 or flat face 126 would impact against the tibial tray 232 and so the impaction force would be applied to the tibial tray 232 rather than the insert 230 and so the insert would not seat properly in the tibial tray 232. Hence, the V-shaped notch provides a fourth formation for providing an impaction force to a fourth component of the knee joint and is specially shaped to engage a particular part of the fourth component to help ensure that the fourth component is also properly impacted. Hence, the second embodiment of the invention provides a single impactor which can be used to help three different components of a knee implant be correctly impacted by engaging four different portions of the different implant components.

The impactor of the present invention has a number of advantages. It helps to reduce the number of instruments that would otherwise be required to perform the same function. It is easier to sterilise than more complex instruments with moving mechanical parts. Indeed, when manufactured from a plastics material, the impactor can be disposable and therefore does not require sterilisation. Further, as neither multiple heads nor multiple impactors are required, the number of instruments in a kit required for the orthopaedic implant is reduced. This further helps to reduce the inventory that needs to be kept by a hospital. Also, there is no need for the surgeon to either change heads or obtain a different instrument during surgery and therefore interruptions to the surgeon's workflow are reduced.

The invention claimed is:

1. A multi-function impactor for use with a knee implant, the knee implant comprising a femoral component, having a first condyle, a second condyle, and an intercondylar notch located between the first condyle and the second condyle and, a tibial component comprising a tibial tray having an upper surface and an insert having an edge and being attachable to the tibial tray, the impactor comprising:
   a shaft having a longitudinal axis, a proximal end and a distal end;
   a head formed at the distal end of the shaft, the head having a front head side at a distal most end of the impactor, a first curved surface formed on the front head side shaped to abut a portion of an outer articular surface of the first condyle of the femoral component, a second curved surface formed on the front head side shaped to abut a portion of an outer articular surface of the second condyle of the femoral component, the second curved surface being spaced from the first curved surface and a planar connecting surface formed on the front head side shaped to abut a portion of the upper surface of the tibial tray, the planar connecting surface having a first portion extending partially around an inner side of the first curved surface facing the longitudinal axis, a second portion extending partially around an inner side of the second curved surface facing the longitudinal axis, and a third portion extending between the first and second portions of the planar connecting surface to connect the first curved surface and the second curved surface,
   wherein the first curved surface is disposed on one side of the longitudinal axis and the second curved surface is disposed on the opposing side of the longitudinal axis, and wherein the first curved surface of the head and the second curved surface of the head are configured to abut the first and second condyles of the femoral component simultaneously;
   the head further comprises a first width extending between two external sides of the first and second curved surfaces away from the longitudinal axis and opposite to the inner sides of the first and second curved surfaces in a direction perpendicular to the longitudinal axis of the shaft;
   a member extending laterally offset from the third portion of the planar connecting surface of the head in a direction perpendicular to the longitudinal axis, the member having a front member side at the distal most end of the impactor, a first member surface formed on the front member side shaped to abut the inter-condylar notch of the femoral component and a concave second member surface formed on the front member side shaped to abut the edge of the insert of the tibial component;
   the member further comprises a second width extending between two opposing edges of the member in a direction parallel to the direction of the first width and perpendicular to the longitudinal axis, wherein the concave second member surface extends across the second width of the member, and wherein the first width is greater than the second width; and
   wherein the head, the member and the shaft are of a monolithic construction.

2. The impactor of claim 1, wherein the first curved surface and the second curved surface are each shaped to provide a best-fit congruent surface for more than one size of the first condyle and the second condyle of the femoral component, respectively.

3. The impactor of claim 1, wherein the planar connecting surface is located distal to the first curved surface and the second curved surface along the longitudinal axis.

4. The impactor of claim 1, wherein the impactor is molded from a plastics material.

* * * * *